United States Patent [19]

Miller et al.

[11] 4,414,210

[45] Nov. 8, 1983

[54] 2-HYDROXYARYLETHYLTRIAZOLE FUNGICIDES

[75] Inventors: George A. Miller, Maple Glen; Hak-Foon Chan, Doylestown, both of Pa.

[73] Assignee: Rohm and Haas Company, Philadelphia, Pa.

[21] Appl. No.: 264,999

[22] Filed: May 19, 1981

Related U.S. Application Data

[60] Continuation of Ser. No. 81,227, Oct. 2, 1979, abandoned, which is a division of Ser. No. 852,125, Nov. 16, 1977, abandoned.

[51] Int. Cl.³ .................. A01N 43/64; A01N 55/02; C07D 249/08; C07F 1/08
[52] U.S. Cl. .................. 424/245; 424/269; 548/101; 548/262; 564/363; 568/645; 568/649; 568/715; 568/808; 568/812
[58] Field of Search .............. 548/101, 262; 424/269, 424/245

[56] References Cited

U.S. PATENT DOCUMENTS 2,776,982  1/1957  Handley .................... 260/348.22
3,394,143  7/1968  Wolf ......................... 548/262

FOREIGN PATENT DOCUMENTS 2431407  1/1976  Fed. Rep. of Germany ...... 548/262
2547954  4/1977  Fed. Rep. of Germany ...... 548/262
2654890  8/1977  Fed. Rep. of Germany ...... 548/262

OTHER PUBLICATIONS

AGDOC 31221Y, 10/27/75, Bayer AG.
AGDOC 31222Y, 10/27/75, Bayer AG.
AGDOC 14368A/08, 7/29/76, ICI.

*Primary Examiner*—Alton D. Rollins
*Attorney, Agent, or Firm*—Polly E. Ramstad; William E. Lambert

[57] ABSTRACT

This invention relates to 2-hydroxyarylethyl-1,2,4-triazoles, their acid addition salts and metal salt complexes. This invention also relates to the method of preparation and use of these compounds. These compounds and salts thereof are highly active broad-spectrum systemic fungicides effective in controlling phytopathogenic fungi such as barley net blotch (*Helminthosporium teres*), grey mold (*Botrytis fabae*), bean powdery mildew (*Erysiphe polygoni*), grape downy mildew (*Plasmopora viticola*), rice blast (*Piricularia oryzae*), tomato late blight (*Phytophthora infestans*) and wheat stem rust (*Puccinia graminis* f. sp. *tritici* race 158-2).

12 Claims, No Drawings

2-HYDROXYARYLETHYLTRIAZOLE FUNGICIDES

This is a continuation of application Ser. No. 081,227 filed Oct. 2, 1979, now abandoned, which is a division of abandoned application Ser. No. 852,125 filed Nov. 16, 1977, now abandoned.

SUMMARY OF THE INVENTION

This invention relates to compounds of the formula $$\begin{array}{c} \text{OH} \quad R^3 \\ | \quad | \\ Z-C-C-W \\ | \quad | \\ R^1 \quad R^2 \end{array} \quad (I)$$

wherein Z is an aryl or substituted aryl group; $R^1$, $R^2$ and $R^3$ are independently a hydrogen atom, a cyano group, an alkyl group, a cycloalkyl group, an alkenyl group, a cycloalkenyl group, an alkynyl group, an aryl or substituted aryl group, an aralkyl or substituted aralkyl group; or $R^1$ and Z when taken together form the group

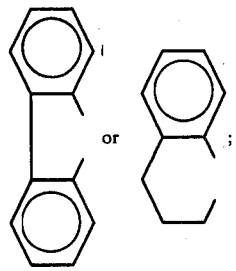

W is a 1 or 4-(1,2,4-triazole); provided that when both $R^2$ and $R^3$ are hydrogen atoms, then $R^1$ is a cyano group, an alkyl group, a cycloalkyl group, an alkenyl group, a cycloalkenyl group, an alkynyl group, an aryl group or a substituted aryl group, an aralkyl or substituted aralkyl group; and the agronomically acceptable acid addition salts and metal salt complexes thereof. This invention also relates to the method of preparation of the compounds and salts of this invention as well as their use as broad-spectrum fungicides.

DETAILED DESCRIPTION OF THIS INVENTION

This invention relates to 1 and 4-hydroxyarylethyl-(1,2,4-triazoles), acid addition salts and metal salt complexes thereof as well as their methods of preparation and use as highly active broad-spectrum systemic fungicides. In particular, this invention relates to compounds of the formula $$\begin{array}{c} \text{OH} \quad R^2 \\ | \quad | \\ Z-C-C-W \\ | \quad | \\ R^1 \quad R^3 \end{array} \quad (II)$$

wherein Z is an optionally substituted ($C_6$ to $C_{10}$) aryl group; $R^1$, $R^2$ and $R^3$ are independently a hydrogen atom, a cyano group, a ($C_1$ to $C_{12}$) alkyl group, a ($C_3$ to $C_8$) cycloalkyl group, a ($C_2$ to $C_8$) alkenyl group, a ($C_5$ to $C_8$) cycloalkenyl group, a ($C_2$ to $C_8$) alkynyl group, an optionally substituted ($C_6$ to $C_{10}$) aryl group, or an optionally substituted ($C_7$ to $C_{11}$) aralkyl group or $R^1$ and Z when taken together form the group

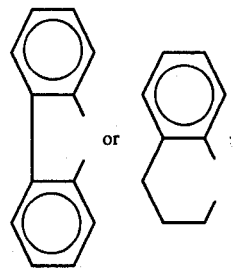

W is a 1 or 4-(1,2,4-triazole); provided that when both $R^2$ and $R^3$ are a hydrogen atom, then $R^1$ is a cyano group, a ($C_1$ to $C_{12}$) alkyl group, a ($C_3$ to $C_8$) cycloalkyl group, a ($C_2$ to $C_8$) alkenyl group, a ($C_5$ to $C_8$) cycloalkenyl group, a ($C_2$ to $C_8$) alkynyl group, an optionally substituted ($C_6$ to $C_{10}$) aryl group, or an optionally substituted ($C_7$ to $C_{11}$) aralkyl group, and the agronomically acceptable acid addition salts and metal salt complexes thereof.

In the definition of the substituents Z, $R^1$, $R^2$ and $R^3$ in the present specification and claims, the term "aryl" is meant to define an aromatic ring structure of from 6 to 10 carbon atoms, preferably a phenyl or naphthyl group which is optionally substituted with up to three substituents, preferably with up to two substituents selected from the group consisting of halogen, nitro, trihalomethyl, cyano, ($C_1$ to $C_4$) alkyl, ($C_1$ to $C_4$) alkylthio, ($C_1$ to $C_4$) alkylsulfinyl, ($C_1$ to $C_4$) alkylsulfonyl, phenoxy, phenylthio, phenylsulfinyl, phenylsulfonyl, and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl. Typical "aryl" and "substituted aryl" groups encompassed by this invention include phenyl, naphthyl, chlorophenyl, bromophenyl, fluorophenyl, iodophenyl, nitrophenyl, trifluoromethylphenyl, trichloromethylphenyl, cyanophenyl, tolyl, anisyl, methylthiophenyl, ethylthiophenyl, methylsulfinylphenyl, methylsulfonylphenyl, phenoxyphenyl, phenylthiophenyl, phenylsulfinylphenyl, phenylsulfonylphenyl, chlorophenoxyphenyl, bromophenoxyphenyl, fluorophenoxyphenyl, iodophenoxyphenyl, nitrophenoxyphenyl, trifluoromethylphenoxyphenyl, 2-cyanophenoxyphenyl, tolyloxyphenyl, anisyloxyphenyl, methylthiophenoxyphenyl, methylsulfinylphenoxyphenyl, methylsulfonylphenoxyphenyl, chlorophenylthiophenyl, bromophenylthiophenyl, fluorophenylthiophenyl, 2-methyl-4-chlorophenyl, 2-bromo-4-trifluoromethylphenyl, 2-methoxy-4-methylsulfonylphenylsulfonylphenyl, 2,4,6-trichlorophenyl, 2-nitro-3,5-dichlorophenyl, 3,4,5-trichlorophenyl, 2,3,4-trichlorophenyl, 2-methyl-4,5-dimethoxyphenyl, 2,4-dimethylsulfonylphenyl, 3,5-diphenoxyphenyl, 2,3-dimethylphenyl, 3,4-difluorophenyl, 2,5-diiodophenyl and the like.

In the definition of the substituents $R^1$, $R^2$ and $R^3$ in the present specification and claims the term "aralkyl" is meant to define an aralkyl group of from 7 to 14 carbon atoms the alkyl portion of which is from 1 to 4 carbon atoms which can be branched or straight chained while the aryl portion is meant to be defined as in the above definition of "aryl". Typical "aralkyl" and "substituted aralkyl" groups encompassed by this invention include benzyl, naphthylmethyl, phenethyl, phenylpropyl, naphthylpropyl, phenylisopropyl, phenylbutyl, naphthylbutyl, phenyl-sec-butyl, phenyl-tert-butyl, phenylpentyl, phenylisopentyl, phenylneopentyl, naphthylmethyl, chlorobenzyl, bromobenzyl, fluorobenzyl, iodobenzyl, nitrobenzyl, trifluoromethylbenzyl, trichloromethylbenzyl, cyanobenzyl, methylbenzyl, methoxybenzyl, methylthiobenzyl, ethylthiobenzyl, methylsulfinylbenzyl, methylsulfonylbenzyl, phenoxybenzyl, phenylthiobenzyl, phenylsulfinylbenzyl, phenylsulfonylbenzyl, chlorophenoxybenzyl, bromophenoxybenzyl, fluorophenoxybenzyl, iodophenoxybenzyl, nitrophenoxybenzyl, trifluoromethylphenoxybenzyl, cyanophenoxybenzyl, tolyloxybenzyl, anisyloxybenzyl, methylthiophenoxybenzyl, methylsulfinylphenoxybenzyl, methylsulfonylphenoxybenzyl, chlorophenylthiobenzyl, bromophenylthiobenzyl, fluorophenylthiobenzyl, 2-methyl-4-chlorobenzyl, 2-bromo-4-trifluoromethylbenzyl, 2-methoxy-4-methylsulfonylphenylsulfonylbenzyl, 2,4,6-trichlorobenzyl, 2-nitro-3,5-dichlorobenzyl, 3,4,5-trichlorobenzyl, 2,3,4-trichlorobenzyl, 2-methyl-4,5-dimethoxybenzyl, 2,4-dimethylsulfonylbenzyl, 3,5-diphenoxybenzyl, 2,3-dimethylbenzyl, 3,4-difluorobenzyl, 2,5-diiodobenzyl and the like.

The term "alkyl" as utilized in the definition of the $R^1$, $R^2$ and $R^3$ substituents in the present specification and claims is meant to define an alkyl group of from 1 to 12 carbon atoms which can be branched or straight chained. Typical alkyl groups encompassed by this invention include methyl, ethyl, propyl, isopropyl, n-butyl, sec-butyl, tert-butyl, n-pentyl, isopentyl, sec-pentyl, neopentyl, n-hexyl, sec-hexyl, heptyl, octyl, nonyl, decyl, undecyl, dodecyl and the like.

The acids which can be utilized in making the acid addition salts of the present invention include hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric, phthalic and the like.

Another embodiment of this invention is the metal salt complexes of the formula

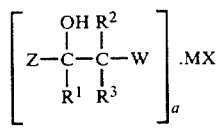

wherein Z, $R^1$, $R^2$ and $R^3$ and W are as defined in Formula (II) above a is an integer from 1 to 4, M is a cation selected from Group IIA, IB, IIB, VIB, VIIB and VIII of the Periodic Table and X is an anion counterion selected in such a manner that the sum of the valence charges of the cation M and the anion X equals zero.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, (mono) or (di) ($C_1$ to $C_4$) alkyldithiocarbamate, ($C_1$ to $C_4$) alkylene-bis-dithiocarbamate and the like.

A preferred embodiment of this invention is the compounds, agronomically acceptable salts and complexes of Formulas (II) and (III) wherein Z is a phenyl or naphthyl group, preferably a phenyl group, optionally substituted with up to three substituents, preferably with up to two substituents, selected from the group consisting of halogen, nitro, trihalomethyl, cyano, ($C_1$ to $C_4$) alkyl, ($C_1$ to $C_4$) alkoxy, ($C_1$ to $C_4$) alkylthio, ($C_1$ to $C_4$) alkylsulfinyl, ($C_1$ to $C_4$) alkylsulfonyl, phenoxy, phenylthio, phenylsulfinyl, phenylsulfonyl, and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl; $R^1$, $R^2$ and $R^3$ are independently a hydrogen atom, a cyano group, a ($C_1$ to $C_8$) alkyl group, a ($C_3$ to $C_6$) cycloalkyl group, a ($C_2$ to $C_4$) alkenyl group, a ($C_5$ to $C_6$) cycloalkenyl group, a ($C_2$ to $C_4$) alkynyl group, a phenyl group optionally substituted with up to two substituents selected from the group consisting of halogen, nitro, trihalomethyl, cyano, methyl, methoxy, methylsulfinyl and methylsulfonyl, or a benzyl or phenethyl group optionally substituted with up to two substituents selected from the group consisting of halogen, nitro, trihalomethyl, cyano, methyl, methoxy, methylthio, methylsulfinyl and methylsulfonyl; or $R^1$ and Z when taken together form the group

provided that when both $R^2$ and $R^3$ are a hydrogen atom, then $R^1$ is a cyano group, a ($C_1$ to $C_8$) alkyl group, a ($C_3$ to $C_6$) cycloalkyl group, a ($C_2$ to $C_4$) alkenyl group, a ($C_5$ to $C_6$) cycloalkenyl group, a ($C_2$ to $C_4$) alkynyl group, a phenyl group optionally substituted with up to two substituents selected from the group consisting of halogen, nitro, trihalomethyl, cyano, methyl, methoxy, methylsulfinyl and methylsulfonyl or a benzyl or phenethyl group optionally substituted with up to two substituents selected from the group consisting of halogen, nitro, trihalomethyl, cyano, methyl, methoxy, methylsulfinyl and methylsulfonyl.

A more preferred embodiment of this invention is the compounds wherein Z is a phenyl group optionally substituted with up to three substituents selected from the group consisting of halogen, preferably chlorine, ($C_1$ to $C_4$) alkyl, preferably methyl and ($C_1$ to $C_4$) alkoxy preferably methoxy; $R^1$ is ($C_1$ to $C_8$) alkyl, phenyl or benzyl; $R^2$ is hydrogen, phenyl or chlorophenyl, preferably hydrogen or 2-chlorophenyl; $R^3$ is hydrogen and W is 1-(1,2,4-triazole).

Typical compounds encompassed by the present invention include:
1-[2-hydroxy-2-methyl-2-(2,4,6-trichlorophenyl)ethyl]-1,2,4-triazole
4-[2-hydroxy-2-n-butyl-2-(2-methyl-4-trifluoromethylphenyl)ethyl]-1,2,4-triazole 1-[2-hydroxy-2-phenyl-2-(3,4-dimethoxyphenyl)ethyl]-1,2,4-triazole
4-[2-hydroxy-2-benzyl-2-(2,3-dichlorophenyl)ethyl]-1,2,4-triazole
4-[2-hydroxy-2-(4-bromophenyl)-2-(3,5-dimethylsulfonylphenyl)ethyl]-1,2,4-triazole
1-[2-hydroxy-1,1-dimethyl-2-(2,4-ditrifluoromethylphenyl)ethyl]-1,2,4-triazole
4-[2-hydroxy-2-phenyl-1-methyl-2-(3,4,5-trimethylphenyl)ethyl]-1,2,4-triazole
1-[2-hydroxy-1,2-bis-n-butyl-2-(2,4-di-tert-butyl phenyl)ethyl]-1,2,4-triazole
4-[2-hydroxy-1,1,2-tris-phenyl-2-(2,4-dichlorophenyl)ethyl]-1,2,4-triazole
1-[2-hydroxy-1,1,2-tris-benzyl-2-(3,4-dinitrophenyl)ethyl]-1,2,4-triazole
4-[2-hydroxy-2-methyl-2-4-(4-methylsulfonylphenyl)sulfonylphenyl ethyl]-1,2,4-triazole
1-[2-hydroxy-2-isopropyl-2-(3-phenoxyphenyl)ethyl]-1,2,4-triazole
4-[2-hydroxy-2-neopentyl-2-(4-phenylthiophenyl)ethyl]-1,2,4-triazole
1-[2-hydroxy-2-sec-hexyl-2-(4-phenylsulfinylphenyl)ethyl]-1,2,4-triazole
4-[2-hydroxy-2-n-heptyl-2-(4-phenylsulfonylphenyl)ethyl]-1,2,4-triazole
1-[2-hydroxy-2-n-octyl-2-4-(4-chlorophenoxy)phenyl ethyl]-1,2,4-triazole
4-[2-hydroxy-2-1-(2-chloronaphthyl)ethyl]-1,2,4-triazole
1-[2-hydroxy-2-2-(1-bromonaphthyl)ethyl]-1,2,4-triazole
4-[2-hydroxy-1,2-dimethyl-2-(2-naphthyl)ethyl]-triazole
1-[2-hydroxy-2-cyclohexyl-2-(2,4,5-trimethoxyphenyl)ethyl]-1,2,4-triazole
4-[2-hydroxy-2-cyclohexenyl-2-(2,4-trichloromethylphenyl)ethyl]-1,2,4-triazole
1-[2-hydroxy-2-cyano-2-(2,4-dinitrophenyl)ethyl]-1,2,4-triazole
4-[2-hydroxy-2-propargyl-2-(2,4-difluorophenyl)ethyl]-1,2,4-triazole
1-[2-hydroxy-2-allyl-2-(2,6-dichlorophenyl)ethyl]-triazole and the agronomically acceptable acid addition salts and metal salt complexes thereof.

The compounds of the present invention can be prepared by general synthetic routes. In particular, the compounds of the present invention can be prepared by the following reaction sequence.

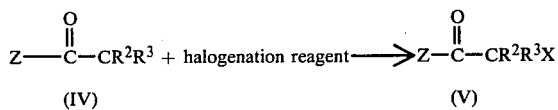

(IV)    (V)

The appropriately substituted acetophenone and methyl-α or β-naphthyl ketone (IV) are readily available starting materials and can be prepared by standard Friedel-Crafts reactions. These ketones can be halogenated with molar or excess amounts of standard halogenation reagents (X) such as chlorine, bromine, N-chlorosuccinimide, N-bromosuccinimide and the like, at temperatures from about 0° C. to about 175° C. either neat or in an appropriate inert solvent such as chloroform, carbon tetrachloride, 1,1,2,2-tetrachloroethane, dichlorobenzene and the like. The resultant α-haloketones (V) are then converted to halohydrins by one of the following reaction sequences.

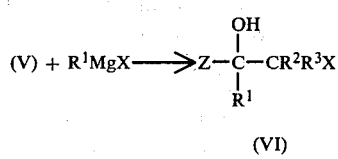

(VI)

The α-haloketone (V) can be converted into a halohydrin by standard Grignard reactions, i.e., by reaction with a molar or excess amount of an aryl or alkyl magnesium halide in an anhydrous inert solvent such as diethyl ether, tetrahydrofuran, dioxane and the like, at temperatures from about −20° C. to about 120° C. followed by acid hydrolysis to give the halohydrin (VI). In the case of highly hindered α-haloketones, reduction takes place instead of alkylation and in such cases the following reaction sequence can be utilized.

The α-haloketones (V) can be converted to the halohydrin as follows:

$(V) + R^1-Li \rightarrow (VI)$

In this reaction the α-haloketone is reacted with a molar or excess amount of an alkyl or aryl lithium organometallic compounds in an anhydrous inert solvent such as hexane, benzene, and the like, at temperatures from about −80° C. to about 30° C. followed by acid hydrolysis to give the halohydrin (VI).

Alternatively, the halohydrins can be prepared by the following reaction sequence.

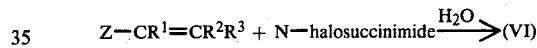

The appropriately substituted ethylene compound is reacted with a molar or excess amount of an N-halosuccinimide, in an appropriate solvent system such as aqueous, ketone or tertiary alcohol systems and the like, at temperatures from about 0° C. to about 150° C. to give the halohydrin (VI) which can then be used in the following reaction sequence.

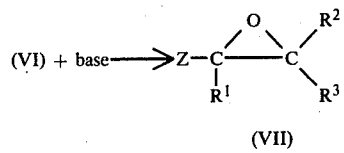

(VII)

The halohydrin (VI) is reacted with a molar amount of a base such as sodium hydroxide, calcium hydroxide and the like or 1,2,4-triazole, either neat or in an appropriate solvent such as dimethylsulfoxide, dimethylformamide and the like at temperatures from about 0° C. to about 150° C. to give the epoxide (VII) which is then used in the following reaction sequence:

$(VII) + W-H \rightarrow (II)$

The epoxide is then reacted with molar or excess amount of 1H-1,2,4-triazole either neat or in an appropriate solvent such as dimethylsulfoxide, dimethylformamide and the like, at temperatures from about 0° C. to about 150° C. to give the compound (II) of the present invention. Alternatively, the halohydrin can be reacted with at least 2 moles of 1H-1,2,4-triazole to form the compound (II) of the present invention without isolating the epoxide (VII) intermediate. When the sodium salt of 1H-1,2,4-triazole is used in the above procedure, only the 1-(1,2,4-triazole) product is obtained whereas the free base gives a mixture of the 1 and 4-(1,2,4-triazoles which can be isolated by standard techniques such as chromatography recrystallization and the like.

Alternatively, the desired product (II) can be prepared from the reaction of a suitably substituted ketone and dimethyl sulfoxonium ylide in an appropriate solvent such as dimethyl sulfoxide at temperatures from about 15° to about 100° to give an epoxide of Formula (VII); which can then be reacted with 1H-1,2,4-triazole as above, to give the desired product.

Starting materials for the above procedures can be prepared by other methods well known in the art and also by procedures described in copending application Ser. No. 840,072 filed on Oct. 6, 1977, now U.S. Pat. No. 4,167,596 by George A. Miller and Hak-Foon Chan which is assigned to a common assignee and incorporated herein by reference.

The acid addition salts of the 2-hydroxyarylethyl-1 or 4-(1,2,4-triazoles) of the present invention can be prepared by standard techniques well-known in the art. For example, the 2-hydroxyarylethyl 1 or 4-(1,2,4-triazole) of Formula (II) can be dissolved in an appropriate solvent such as diethyl ether, tetrahydrofuran, ethanol, methanol and the like or combinations thereof, and treated with an equivalent or excess amount of a mineral or organic acid which may or may not be dissolved in a similarly appropriate solvent. The mixture is then either cooled or evaporated to give the salt which can either be used as such or recrystallized from an appropriate solvent or combination of appropriate solvents.

The metal salt complexes of the above 2-hydroxyarylethyl 1 or 4-(1,2,4-triazoles) can be prepared by adding dropwise, with stirring, a stoichiometric amount of a metal salt dissolved in an appropriate solvent or combination of solvents to a solution of the 2-hydroxyarylethyl 1 or 4-(1,2,4-triazole) of Formula (II) dissolved in a similarly appropriate solvent or combination of solvents. The reaction mixture is briefly stirred and the solvent is removed under reduced pressure to give the metal salt complex of the respective 2-hydroxyarylethyl 1 or 4-(1,2,4-triazole) of Formula (III).

The metal salt complexes can also be prepared by mixing stoichiometric or excess amounts of the metal salt and a 2-hydroxyarylethyltriazole of Formula (II) in the desired amount of solvent containing appropriate adjuvants just prior to spraying the plants. Adjuvants that may be included in the "in-situ" preparation may be detergents, emulsifiers, wetting agents, spreading agents, dispersing agents, stickers, adhesives, and the like which are used in agricultural applications.

Solvents that can be utilized in these procedures include any polar solvent, e.g., water, methanol, ethanol, isopropanol, or ethylene glycol and any aprotic dipolar solvent, e.g., dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium, and the like.

Any appropriate anion, e.g., chloride, bromide, iodide, sulfate, bisulfate, phosphate, nitrate, perchlorate, carbonate, bicarbonate, hydrosulfide, hydroxide, acetate, oxalate, malate, citrate, tartarates, maleate and the like may be utilized as the counterion in the metal salt.

Any metal containing fungicides can also be used as complexing agents used in place of metal salts. Typical metal containing fungicides that can be utilized in these procedures are: (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); (b) copper-based fungicides such as cuprous oxide, copper oxychloride, copper naphthenate, and Bordeaux mixture; and (c) miscellaneous fungicides such as: phenylmercuri acetate, N-ethyl-mercuri-3,4,5,6,7,7-hexachlorophthalimide, phenylmercuri monoethanolammonium lactate, nickel-containing compounds and calcium cyanamide.

The compounds of this invention possess an assymetric carbon atom and as made are racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees centigrade.

EXAMPLE 1

Preparation of 1-[2-hydroxy-2-(2,4-dichlorophenyl) hexyl]1,2,4-triazolium nitrate A. 2-Hydroxy-2-(2,4-dichlorophenyl) hexyl chloride Into a 500 ml four-necked flask equipped with a low temperature condenser, a mechanical stirrer, an additional funnel and a nitrogen inlet tub, are placed 102 ml (0.2 m) of n-butyl lithium. This solution is cooled to $-60°$ with an acetone-dry ice bath. A solution of 45 g (0.2 m) of 2,4-dichlorophenacyl chloride dissolved in 250 ml of dry ether is added dropwise. A constant flow of dry nitrogen is maintained throughout the addition. The rate of addition is adjusted so that the reaction temperature does not exceed $-55°$. After the addition, the reaction is gradually warmed to $-10°$ and then poured into 500 ml of a mixture of saturated ammonium chloride solution and 10% hydrochloric acid solution. The organic layer is separated and the aqueous layer is further extracted with 100 ml of ether. The combined organic extracts are washed with 10% hydrochloric acid and dried over $MgSO_4$. Solvent is evaporated to give 52 g of a pale yellow oil. This material is further purified by vacuum distillation (110°–120°/0.2 mm) to give 44 g of pure product.

nmr(CDCl): δ0.6–2.6 (complex multiplets, 9H), 2.8 (S, 1H, concentration dependent), 4.3 (q, 2H), 7.1–7.9 (m, 3H).

B. 1-[2-Hydroxy-2-(2,4-dichlorophenyl) hexyl]-1,2,4-triazolium nitrate

To a dimethyl sulfoxide solution (30 ml) of sodium 1,2,4-triazole, generated from 1.12 g (0.017 m) of 1H-1,2,4-triazole and 0.68 g (0.017 m) of sodium hydroxide, is added 3.3 g (0.015 m) of 2-hydroxy-2-(2,4-dichlorophenyl) hexyl chloride in 20 ml of dimethyl sulfoxide dropwise at 110° under nitrogen.

The brown reaction mixture is stirred at 110° for an additional hour. It is then poured into 400 ml of water and extracted with methylene chloride. The combined methylene chloride extracts are washed with water and dried over MgSO$_4$. Solvent is evaporated to give 2.8 g of a light yellow oil. This material is redissolved in 300 ml of a 50—50 ether-hexane mixture and converted to its nitric acid salt in the usual manner. A total of 1 g of light yellow solid is obtained.

nmr (DMSO): δ0.6–2.1 (complex multiplets, 9H), 4.9 (q, 2H), 6.1 (S, 1H), 7.2–8.0 (m, 3H), 8.6 (S, 1H), 9.4 (S, 1H), 9.6 (S, 1H).

EXAMPLE 2

Preparation of 1-(2-hydroxy-2-phenylhexyl)-1,2,4-triazole and 4-(2-hydroxy-2-phenylhexyl)-1,2,4-triazole

A. 2-Phenyl-1,2-epoxyhexane

Into a 500 ml four-necked flask equipped with a low temperature condenser, a mechanical stirrer, an addition funnel, and a nitrogen inlet tube, are placed 125 ml (1.97 molar in hexane) of n-butyl lithium (0.246 mole). This solution is cooled to −60° with an acetone-dry ice bath. A solution of 49 g (0.246 mole) of phenacyl bromide in 250 ml of anhydrous ether is added dropwise. A constant flow of dry nitrogen is maintained throughout the addition. The rate of addition is adjusted so that the reaction temperature does not exceed −60°. The reaction mixture is stirred for 2 hours and then poured into 500 ml of a mixture of saturated NH Cl solution and 10% HCl solution. The organic layer is separated and the aqueous layer is extracted with ether. The combined organic extracts are washed with water, saturated NaCl solution, and dried over MgSO$_4$. Solvent is evaporated to give 36.8 g of crude product. Nmr analysis reveals this material to be 2-phenyl-1,2-epoxyhexane.

nmr (CDCl): δ0.6–2.1 (m, 9H), 2.8 (q, 2H), 7.35 (m, 5H).

B. 1-[2-Hydroxy-2-phenylhexyl]-1,2,4-triazole and 4-(2-hydroxy-2-phenylhexyl)-1,2,4-triazole A mixture of 10 g (0.057 mole) of 2-phenyl-1,2,-epoxyhexane and 10 g (0.015 mole) of 1H-1,2,4-triazole is heated at 160° overnight. The reaction mixture is cooled, poured into water, and extracted with ether. The combined ether extracts are washed with water and dried over MgSO$_4$. The product obtained is further purified by converting to its HNO$_3$ salt and then back neutralized with sodium bicarbonate solution to give 3.6 g of product. Glc and nmr analyses reveal this material to be a mixture of 1-(2-hydroxy-2-phenylhexyl)-1,2,4-triazole and 4-(2-hydroxy-2-phenylhexyl)-1,2,4-triazole in a 4:1 ratio.

nmr (CDCl$_3$): δ0.6–2.1 (m, 9H), 4.1–4.6 (m, 2H), 4.8–5.2 (broad, S, 1H), 7.0–8.2 (m, with S at 7.7, 7.9, and 8.2, 7H).

EXAMPLE 4

Preparation of 1-[2-hydroxy-2-(2,4-dichlorophenyl) ethyl]-1,2,4-triazole

A. 2-Hydroxy-2,4-dichlorophenethyl chloride

To a solution of 52 g (0.23 m) of 2,4-dichlorophenacyl chloride in 200 ml of dioxane is added 9 g (0.24 m) of sodium borohydride dissolved in 60 ml of water dropwise at 50°. The addition is set at such a rate that the reaction temperature does not exceed 50°. After the addition, the reaction mixture is stirred at 50° for 1½ hours. Excess sodium borohydride is carefully decomposed by slow addition of 10% hydrochloric acid. The organic product is extracted into ether and the combined ether extracts are washed with water, saturated sodium bicarbonate solution, and dried over MgSO$_4$. Solvent is evaporated to give 49 g of product.

B. 1-[2-Hydroxy-2-(2,4-dichlorophenyl) ethyl]-1,2,4-triazole

To a dimethyl sulfoxide solution (50 ml) of sodium 1,2,4-triazole, generated from 3.25 g (0.047 m) of 1H-1,2,4-triazole, and 1.9 g (0.047 m) of sodium hydroxide, is added 10 g (0.045 m) of 2-hydroxy-2,4-dichlorophenethyl chloride dropwise at 110° under nitrogen. The reaction is stirred at 110° for 1½ hours. The reaction mixture is poured into water and extracted with methylene chloride. The combined organic extracts are washed with water and dried over MgSO$_4$. Solvent is evaporated to give 8 g of product.

nmr (CDCl$_3$): δ4.4 (d, 2H), 5.4 (m, 1H), 6.1 (d, 1H, exchangeable with D$_2$O), 7.7 (m, 3H), 8.0 (S, 1H), 8.5 (S, 1H).

EXAMPLE 6

Preparation of 4-[2-hydroxy-2-(2,4-dichlorophenyl) ethyl]-1,2,4-triazole

A. 2-Hydroxy-2,4-dichlorophenethyl amine

Anhydrous ammonia is bubbled into 50 ml of absolute ethanol in a pressure bottle for 10 minutes until it is saturated. A sample of 35 g of 1,2-epoxyethyl-2,4-dichlorobenzene is then added and the mixture is heated at 90° overnight. The crude is then dissolved in 300 ml of ether and the hydroxy amine is converted to its hydrochloride salt by bubbling dry hydrogen chloride gas through. The hydrochloride salt collected is back neutralized to its free base with diluted ammonium hydroxide solution to give 21 g of desired product.

B. 4-[2-Hydroxy-2-(2,4-dichlorophenyl) ethyl]-1,2,4-triazole

A mixture of 1.5 g (0.007 m) of 2-hydroxy-2,4-dichlorophenethyl amine, 1.5 g (0.01 m) of N,N-dimethylformamide azine, 0.5 g of toluene p-sulfonic acid in 50 ml of toluene is heated under reflux overnight. Solvent is evaporated under reduced pressure. The residue is taken up in methylene chloride and the free base is purified by converting it to its hydrochloride salt and back neutralized with ammonium hydroxide solution to give 1.5 g of product.

nmr (DMSO): δ4.5 (m, 2H), 5.3 (t, 1H), 6.5 (broad, S, 1H, exchangeable with D$_2$O), 7.6 (m, 3H), 8.6 (S, 2H).

EXAMPLE 8

Preparation of 1-[2-hydroxy-2-(p-tolyl) propyl]-1,2,4-triazole nitric acid salt

To 75 ml of dried-distilled dimethylsulfoxide (DMSO) is slurried 3.6 g (0.0735 mole) of 50% sodium hydroxide. To this mixture is added portionwise under nitrogen 15.2 g (0.069 mole) of trimethyl sulfoxonium iodide, and H$_2$ gas is soon evolving. When the addition is complete, the slurry is stirred for 1 hour. Then 7.5 g (0.056 mole) of p-methyl acetophenone is added and the stirring is continued for an additional hour. After heating this mixture at 50°–60° for 3 hours, it is cooled and let stand.

To 50 ml of DMSO is added 5.5 g (0.08 mole) of 1H-1,2,4-triazole and 3.1 g (0.078 mole) of sodium hydroxide. After warming, a solution formed. To this is added 75 ml of toluene, and the mixture is heated to reflux, and water is azeotroped. When the water stopped azeotroping, the toluene is stripped to leave a DMSO solution of the imidazole sodium salt. This solution is cooled and added to the first DMSO solution prepared earlier.

The reaction is warmed to 80° for 3 hours and cooled before it is poured into water. The crude product, which oils out, is extracted with methylene chloride, and the extract is dried over anhydrous magnesium sulfate and concentrated to yield 7.4 g (60.9%) of the crude product. This material is dissolved in ether, and the solution is treated with concentrated nitric acid, and after stirring the solid salt forms. This material is separated by filtration, and recrystallized from acetone-ether to give 2.8 g (23%) of the product, mp 140°-2°.

EXAMPLE 11

Preparation of Zinc chloride complex of 1-[2-hydroxy-2-(p-methoxyphenyl)-3-phenylpropyl]-1,2,4-triazole To 1.0 g (0.00268 mole) of 1-[2-hydroxy-2-(p-methoxyphenyl)-3-phenylpropyl]-1,2,4-triazole nitric acid salt in 50 ml of methanol is first added 0.2 g (0.00268 mole) of 50% sodium hydroxide and then 0.4 g (0.00293 mole) of zinc chloride. The yellow tinted solution is stirred for ¼ hour, and then the methanol is distilled. The residue is stirred with 50 ml of warm water. The water was decanted, and the organic material is dissolved in warm benzene. The solution is dried over anhydrous magnesium sulfate, and the benzene is distilled to give 0.6 g (56.8% yield) of the amorphous solid product, mp 70°-3°.

EXAMPLE 12

Preparation of 1,2,3,4-tetrahydro-1-hydroxy-1[1-(1,2,4-triazolyl)methyl]-naphthalene To 20.92 g (0.227 mole) of dimethyl oxosulfonium methylide in 175 ml of DMSO (preparation described in Example 8) under nitrogen is added dropwise with stirring 26.8 g (0.183 mole) of 1-tetralone in 75 ml of DMSO. When the addition is complete (0.5 hr.), the reaction is warmed to 55° for 2 hours and then it is allowed to stir at ambient temperature for 16 hours.

At the end of this period the reaction is poured into a liter of water. The organic material is extracted 2×150 ml of ether and the extract is washed 2×50 ml of water, dried over anhydrous magnesium sulfate and concentrated at ambient temperature to give 20.8 g of crude spiro (1,2,3,4-tetrahydronaphthalene-1,2-oxiran).

To 5.8 g (0.06423 mole) of the sodium salt of 1H-1,2,4-triazole (prepared from 4.4 g; 0.06423 mole of triazole and 2.57 g, 0.06423 mole of NaOH) in 75 ml of DMSO is added dropwise at 110°-15°, 10.4 g (0.0649 mole) of the spiro (1,2,3,4-tetrahydro-naphthalene-1,2-oxiran). When the addition is complete, the reaction is held at 115° for another ½ hour and then it is cooled.

The reaction material is mixed with 150 ml of water, and the organic material which separated is extracted with 150 ml of ether. The extract is washed 2×50 ml of water, dried over anhydrous magnesium sulfate, and concentrated to give the crude product as an oil. This material is dissolved in ether, and upon treatment with hydrogen chloride gas the product salt precipitated. The material is dried to give 5.6 g (32.5%) of the hydrochloride salt, mp 179°-80°.

To 3.5 g (0.0132 mole) of 1,2,3,4-tetrahydro-1-hydroxy-1-[1-(1,2,4-triazolyl)methyl]-naphthalene hydrochloride in 200 ml of water is added 2.0 g (0.025 mole) of 50% NaOH, and the mixture is stirred. The organic material is extracted 2×100 ml of ether, and the extract is washed 2×50 ml of water, dried over anhydrous magnesium sulfate, and concentrated to give 2.6 g (85.9%) of the product, mp 105°-8°.

Tables I and II give the structure, melting points in degrees centigrade and the elemental analysis of some of the more representative compounds encompassed by the present invention which were synthesized by the above procedures.

TABLE I $$Z-\underset{\underset{R^1}{|}}{\overset{\overset{OH}{|}}{C}}-CH_2-W.Y$$

| Example # | Z | R₁ | W | Y |
|---|---|---|---|---|
| 1 | 2,4-ClC₆H₃ | C₄H₉n | 1-triazole | HNO₃ |
| 2 | C₆H₅ | C₄H₉ | 1&4-triazole | — |
| 3 | C₆H₅ | H | 1-triazole | — |
| 4 | 2,4-ClC₆H₃ | H | 1-triazole | — |
| 5 | 2,4-ClC₆H₃ | H | 1-triazole | HNO₃ |
| 6 | 2,4-ClC₆H₁₃ | H | 4-triazole | — |
| 7 | C₆H₅ | C₈H₁₇ | 1-triazole | HNO₃ |
| 8 | 4-CH₃C₆H₄ | CH₃ | 1-triazole | HNO₃ |
| 9 | 4-CH₃OC₆H₄ | CH₂C₆H₅ | 1-triazole | — |
| 10 | 4-CH₃OC₆H₄ | CH₂C₆H₅ | 1-triazole | HNO₃ |
| 11 | 4-CH₃OC₆H₄ | CH₂C₆H₅ | 1-triazole | ½ ZnCl₂ |
| 12 | Z + R¹ = 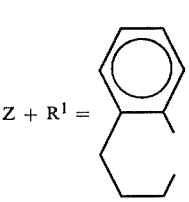 | | 1-triazole | — |
| 13 | Z + R¹ = 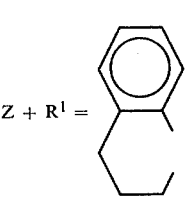 | | 1-triazole | HCl |

TABLE II

| | | Elemental Analysis: Calc'd (Found) | | | | | |
|---|---|---|---|---|---|---|---|
| Example No. | MP° | C | H | Cl | N | O | Zn |
| 1 | 97-9 | 44.58(42.08) | 4.81(4.04) | 18.80(20.12) | 14.85(15.21) | 16.96(18.33) | |
| 2 | oil | 68.54(71.02) | 7.81(8.05) | | 17.13(16.24) | | |
| 3 | 118-20 | 63.43(63.40) | 5.86(6.08) | | 22.21(22.14) | | |

TABLE II-continued

| Example No. | MP° | C | H | Cl | N | O | Zn |
|---|---|---|---|---|---|---|---|
| 4 | 92–3 | 46.54(46.70) | 3.51(3.50) | 27.47(27.85) | 16.28(16.49) | 6.20(6.46) | |
| 5 | 168–70 | 37.40(38.44) | 3.14(3.22) | 22.08(22.61) | 17.45(16.60) | 19.93(19.26) | |
| 6 | 112–4 | 46.54(45.51) | 3.51(3.58) | 27.47(27.20) | 16.28(15.91) | 6.20(6.77) | |
| 7 | 119–21 | 59.32(58.98) | 7.74(7.84) | | 15.37(15.93) | 17.56(17.91) | |
| 8 | 140–2 | 51.42(51.27) | 5.75(5.72) | | 19.99(20.01) | 22.83(21.70) | |
| 9 | 188–90 | 74.00(74.03) | 6.54(6.51) | | 9.09(9.46) | 10.38(10.72) | |
| 10 | 149–50 | 58.95(56.19) | 5.41(5.23) | | 15.05(15.89) | 21.48(22.15) | |
| 11 | 70–3 | 57.27(58.35) | 5.07(5.19) | 9.39(7.46) | 11.13(11.79) | 8.48(10.86) | 8.66(6.21) |
| 12 | 105–8 | 68.10(68.35) | 6.59(6.80) | | 18.33(16.17) | 6.98(8.00) | |
| 13 | 179–80 | 58.76(59.22) | 6.07(6.42) | 13.34(11.60) | 15.81(14.56) | 6.02(7.96) | |

The 1&4-(2-hydroxyarylethyl) 1,2,4-triazoles, acid addition salts and metal salt complexes of this invention are broadspectrum fungicides which possess a high degree of activity against assorted phytopathogenic fungi. These compounds, salts and complexes are particularly effective at rates of application from about 50 to about 2000 ppm in controlling barley net blotch (*Helminthosporium teres*) on barley plants, grey mold (*Botrytis fabae* on faba beans, bean powdery mildew (*Erysiphe poilygoni*) on bean plants, grape downy mildew (*Plasmopora viticola*) on grape seedlings, rice blast (*Piricularia oryzae*) on rice plants, tomato late blight (*Phytophthora infestans*) on tomato seedlings, and wheat stem rust (*Puccinia graminis* f. sp. tritici race 15B-2) on wheat seedlings.

In evaluating these compounds, a preliminary fungicidal evaluation is carried out using the compounds at 300 ppm and spraying the plants to run off in a carrier volume of about 150 gallons/acre.

The general procedure is to take potted plants in proper condition of growth for susceptibility to the fungal disease to be evaluated, to spray these on a moving belt and alow them to dry. The proper plants are then inoculated with the fungal spores and then allowed to incubate until the disease has developed and the percent control is read or estimated.

The following test methods are employed in evaluating the fungicidal activity of the compounds, salts and complexes of this invention.

EXAMPLE A

BARLEY NET BLOTCH (*Helminthosporium teres*)

Barley plants (var. Wong) are trimmed to a height of approximately 2.5 inches, 24 hours prior to chemical application. This procedure provides plants of a uniform height and permits rapid rapid inoculation of treated plants. The barley plants are inoculated by spraying the foilage of the plants with a hand sprayer until small droplets of the inoculum are observed on the leaves. Inoculated plants are incubated in a humid environment at 75°–80° F. for 24 hours prior to being placed in the greenhouse at 70°–75° F. Treatment comparisons are made 6 to 7 days after inoculation. Typical barley net blotch symptoms initially appear as irregular sunken water-soaked areas which become necrotic as the lesions enlarge. Certain of the 1-(2-hydroxyarylethyl)-1,2,4-triazoles of this invention demonstrate greater than 70% control over *Helminthosporium teres* at application rates of 300 ppm.

EXAMPLE B

Broad Bean Gray Mold Leaf Spot (*Botrytis fabae*)

Broad bean plants (var. Vicia faba) are trimmed to a height of approximately 4.5 inches, 24 hours prior to chemical application. This procedure provides plants of a uniform height and permits rapid and uniform inoculation of the treated plants. Broad bean plants are inoculated by spraying the foilage with a herbicide belt sprayer. Inoculated plants are incubated in a humid environment at 75°–80° F. for 66 hours. Treatment comparisons are made 66 to 68 hours after inoculation. Typical broad bean gray mold leaf spot symptoms appear as regular circular to lanceolate lesions on plant leaves and stems. Certain of the 1-(2-hydroxyarylethyl)-1,2,4-triazoles of this invention demonstrate complete control over *Botrytis fabae* at application rates of 300 ppm.

EXAMPLE C

Bean Powdery Mildew (*Erysiphe polygoni*)

Bean plants (var. Dwarf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildew symptoms are circular white mycelial mats (fructifications) on the leaf surface. Certain of the 1-(2-hydroxyarylethyl)-1,2,4-triazoles of this invention demonstrate complete control over *Erysiphe polygoni* at application rates greater than 300 ppm.

EXAMPLE D

Grape Downy Mildew *Plasmopora viticola*)

Grape seedlings (var. Siebel 1000) 4 to 5 inches tall are used. *Plasmopora viticola* is cultured on grape leaves for 7 days at 65°–75° F. The grape plants are inoculated by spraying the leaves with a hand held air brush until small uniform droplets of inoculum are observed on the leaves. The inoculated plants are incubated in a humid environment at 65°–70° F. for 48 hours prior to being placed in a growth room. Typical grape downy mildew symptoms appear on the upper surface as pale-yellow spots variable in size and form, frequently circular without a distinct line of demarcation. Under humid conditions the lower leaf surface is covered by conspicuous fungal growth. Certain of the 1-(2-hydroxyarylethyl)-1,2,4-triazoles of this invention possess complete control over *Plasmopora viticola* at application rates of 300 ppm.

EXAMPLE E

Rice Blase (*Piricularia oryzae*)

Rice plants (var. Nova 66) are trimmed to a height of approximately 5 inches, 24 hours prior to chemical application. This procedure provides plants of uniform height and permits rapid inoculation of treated plants. Rice plants are inoculated by spraying the leaves and stems with an air brush until a uniform film of inoculum is observed on the leaves. The inoculated plants are incubated in a humid environment (75°-85° F.) for 24 hours prior to being placed in a greenhouse environment. Treatment comparisons are made 7 to 8 days after inoculation. Initial rice blast lesions appear as small brown necrotic spots on the foilage. The typical lesion is ecliptical, 1 to 2 cm. long with a large necrotic gray center and brown margins. Certain of the 1&4-(2-hydroxyarylethyl)-1,2,4-triazole of this invention possess complete control over *Piricularia oryzae* at application rates of 300 ppm.

EXAMPLE F

Tomato Late Blight (*Phytophthora infestans*)

Tomato (var. Rutgers) seedlings, 2.5 to 3 inches tall, are fertilized with a water soluble fertilizer 4 to 5 days prior to chemical application to promote rapid succulent growth and better symptom expression. The spore suspension is applied with a DeVilbiss atomizer at 8 to 10 psi. air pressure onto the leaf undersurface until fine droplets are formed. Inoculated seedlings are placed in a humid environment at 60°-62° F. for 40 to 45 hours, prior to being placed in the greenhouse at 70°-75° F. Treatment comparisons are made 5 to 6 days after inoculation. Initially, typical tomato late blight symptoms appear as irregular, greenishblack, water-soaked patches which enlarge and become brown, with a firm corrugated surface. Severe infection will resemble frost damage. Certain of the 1-(2-hydroxyarylethyl)-1,2,4-triazoles of the present invention possess complete control over *Phytophthora infestans* at application rates of 300 ppm.

EXAMPLE G

Wheat Stem Rust (*Puccinia graminis* f. sp. tritici race 15B-2)

Seven-day-old wheat plants (var. Monon) are trimmed to approximately 2.5 inches, 24 hours prior to chemical application to provide a uniform plant height and to facilitate uniform inoculation. Wheat stem rust is cultured on wheat seedlings (var. Monon) for a period of 14 days under existing greenhouse conditions. Wheat plants are inoculated by applying the stem rust spore suspension, until run-off, with a DeVilbiss atomizer at 5 psi. air pressure. After inoculation, the plants are placed into a humid environment at approximately 68° F. A timer is used to permit 12 hours of continuous darkness followed by a minimum of 3 to 4 hours of light with an intensity of 500 foot candles. The temperature in the chamber should not exceed 85° F. At the end of the light period, the fogger is turned off and vented to allow the plants to dry slowly prior to being placed into a greenhouse environment. The plants are permitted to grow under greenhouse conditions for a period of 2 weeks prior to making treatment comparisons. Wheat stem rust is characterized by brick red spores in irregularly shaped sori on the leaves and stems of the wheat seedlings. Certain of the 1&4-(2-hydroxyarylethyl)-1,2,4-triazoles of the present invention possess complete control over *Puccinia graminis* f. sp. tritici race 15B-2 at application rates of 300 ppm.

The 1&4-(2-hydroxyarylethyl)-1,2,4-triazoles, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in an agronomically acceptable carrier or are formulated so as to render them suitable for subsequent dissemination as fungicides. For example, these chemical agents can be formulated as wettable powders, emulsifiable concentrated, dusts, granular formulations, aerosols, or flowable emulsion concentrates. In such formulations, the compounds are extended with a liquid or solid carrier and, when desired, suitable surfactants are incorporated.

By the term "agronomically acceptable carrier" is meant any substance which can be utilized to dissolve, disperse, or diffuse the chemical agent incorporated therein without impairing the effectiveness of the chemical agent and which does no permanent damage to such environment as soil, equipment and agronomic crops.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual".

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 1-[2-hydroxy-2-(2,4-dichlorophenyl)hexyl]-1,2,4-triazole, 45 parts of a synthetic precipitated hydrated silicon dioxide sold under the trademark Hi-Sil, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate solid under the trademark Zeolex 7.

Dusts are prepared by mixing the 1&4-(2-hydroxyarylethyl)-1,2,4-triazoles, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The 1&4-(2-hydroxyarylethyl)-1,2,4-triazoles, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention include:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zine ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrazohydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimido-phosphorothioate, 4-butyl-1,2,4-triazole, 5-amino-1bis(dimethylamino)-phosphinyl-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-4,5-b quinoxaline (thioquinox), methyl 1-(butylcarbamoyl)-2-benzimidazole carbamate (benomyl), 2-(4'-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, -(phenyl)- -(2,4-dichlorophenyl)-5-pyrimidinyl-methanol (triarimol), cis-N-(1,1,2,2-tetrachloroethyl)thio-4-cyclohexene-1,2-dicarboxyimide, 3-2-(3,5-dimethyl-2-oxycyclohexyl-2-hydroxy-glutarimide (cycloheximide), dehydroacetic acid, N-(1,2,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo 4,5-b-quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthaneate, and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7,-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido) benzene (thiophanate-methyl).

The 1&4-(2-hydroxyarylethyl)-1,2,4-triazoles, addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the 1&4-(2-hydroxyarylethyl)-1,2,4-triazoles of this invention will suggest themselves to those skilled in the art of agriculture and horticulture.

We claim:

1. A compound of the formula

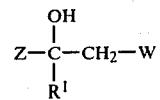

wherein

Z is an unsubstituted phenyl or naphthyl group or a phenyl or naphthyl group substituted with up to three substituents selected from the group consisting of halogen, nitro, trihalomethyl, cyano, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl, phenoxy, phenylthio, phenylsulfinyl, phenylsulfonyl and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl;

R$^1$ is cyano (C$_3$-C$_{12}$)alkyl, (C$_3$-C$_8$)cycloalkyl, (C$_2$-C$_8$)alkenyl, (C$_5$-C$_8$)cycloalkenyl, (C$_2$-C$_8$)alkynyl, unsubstituted phenyl or phenyl substituted with up to two substituents selected from the group consisting of halogen, nitro, trihalomethyl, cyano, methyl, methoxy, methylsulfinyl and methylsulfonyl; or unsubstituted benzyl or phenethyl, or benzyl or phenethyl substituted with up to two substituents selected from the group consisting of halogen, nitro, trihalomethyl, cyano, methyl, methoxy, methylthio, methylsulfinyl, and methylsulfonyl; and W is a 1 or 4-(1,2,4-triazole);

and the agronomically acceptable acid addition salts and metal said complexes thereof.

2. The compound of claim 1 wherein R$^1$ is (C$_3$-C$_8$)alkyl, (C$_3$-C$_6$)cycloalkyl, (C$_2$-C$_4$)alkenyl, (C$_5$-C$_6$)cycloalkenyl, (C$_2$-C$_4$)alkynyl, unsubstituted phenyl or phenyl substituted with up to two substituents selected from the group consisting of halogen, nitro, trihalomethyl, cyano, methyl, methoxy, methylsulfinyl and methylsulfonyl; or unsubstituted benzyl or phenethyl, or benzyl or phenethyl substituted with up to two substituents selected from the group consisting of halogen, nitro, trihalomethyl, cyano, methyl, methoxy, methylthio, methylsulfinyl, and methylsulfonyl; and W is 1-(1,2,4-triazole).

3. A compound of the formula

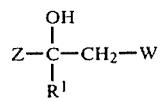

wherein Z is unsubstituted phenyl or phenyl substituted with up to three substituents selected from the group consisting of halogen, (C$_1$-C$_4$)alkyl and (C$_1$-C$_4$)alkoxy; R$^1$ is (C$_4$-C$_8$)alkyl, phenyl or benzyl; and W is 1-(1,2,4-triazole).

4. The compound of claim 3 wherein Z is unsubstituted phenyl or phenyl substituted with up to two substituents selected from the group consisting of chloro, methyl and methoxy; and R$^1$ is n-butyl, n-octyl, benzyl or phenyl.

5. The compound of claim 4 wherein Z is phenyl, 4-methylphenyl, 2,4-dichlorophenyl or 4-methoxyphenyl; R$^1$ is n-butyl, n-octyl, phenyl or benzyl.

6. The compound of claim 5 having the structure

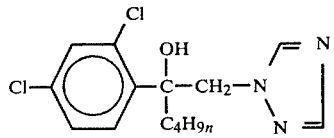

7. The compound of claim 5 having the structure

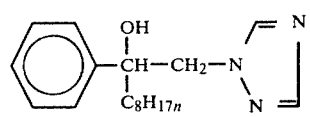

and the agronomically acceptable acid addition salts and metal salt complexes thereof.

8. The compound of claim 5 having the structure

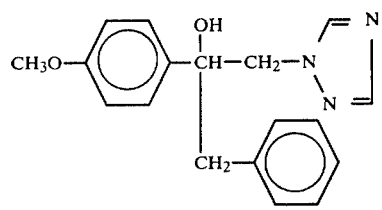

and the agronomically acceptable acid addition salts and metal salt complexes thereof.

9. The compound of claim 5 having the structure

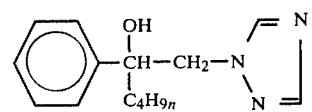

and the agronomically acceptable acid addition salts and metal salt complexes thereof.

10. The compound of claim 1 having the structure

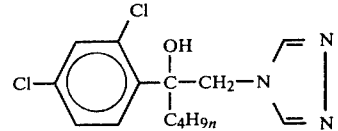

and the agronomically acceptable acid addition salt and metal salt complexes thereof.

11. A fungicidal composition which comprises, an agronomically acceptable carrier and as the active ingredient, a fungicidally effective amount of a compound according to claim 2.

12. A method for controlling phytopathogenic fungi which comprises, applying to the plant, the plant seed or the plant habitat a fungicidally effective amount of a compound according to claim 2.

* * * * *

UNITED STATES PATENT AND TRADEMARK OFFICE
CERTIFICATE OF CORRECTION

PATENT NO. : 4,414,210
DATED : November 8, 1983
INVENTOR(S) : George A. Miller et al.

It is certified that error appears in the above—identified patent and that said Letters Patent is hereby corrected as shown below:

Front Cover, last line of Abstract, "15B-2" should read
-- 15B-2 --.
Column 10, line 61, "hydroxide" should read -- hydride --.
Column 13, line 28, "poilygoni" should read -- polygoni --.
Column 13, line 42, "alow" should read -- allow --.
Column 13, line 55, delete second occurrence of "rapid".
Column 13, line 57, "foilage" should read -- foliage --.
Column 14, line 25, "foilage" should read -- foliage --.
Column 15, line 2, "Blase" should read "Blast".
Column 15, line 15, "foilage" should read -- foliage --.
Column 16, line 15, "concentrated" should read
-- concentrates --.
Column 17, line 34, "zine" should read -- zinc --.

Column 19, line 20, "metal said" should read -- metal salt --.
Column 18, line 26, "naphthaneate" should read -- naphthenate --.

Column 20, claim 7, structure

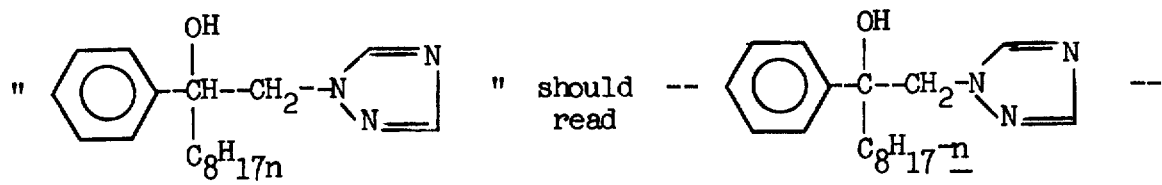

UNITED STATES PATENT AND TRADEMARK OFFICE
CERTIFICATE OF CORRECTION

PATENT NO. : 4,414,210
DATED : November 8, 1983
INVENTOR(S) : George A. Miller et al.

It is certified that error appears in the above—identified patent and that said Letters Patent is hereby corrected as shown below:

Column 20, claim 8, structure

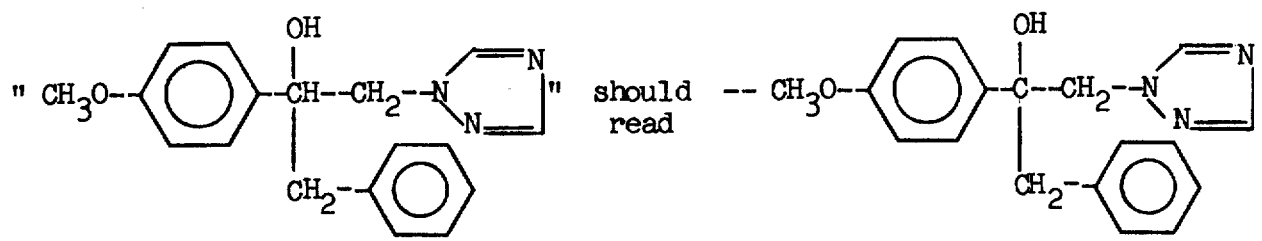

Column 20, claim 9, structure

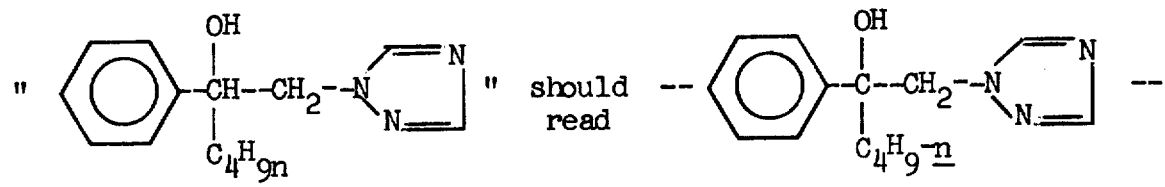

Signed and Sealed this

Twenty-third Day of October 1984

[SEAL]

Attest:

Attesting Officer

GERALD J. MOSSINGHOFF
Commissioner of Patents and Trademarks